US012788623B2

(12) United States Patent
Zhu

(10) Patent No.: US 12,788,623 B2
(45) **Date of Patent: *Nov. 10, 2026**

(54) COMBINED TYPE HAND WARMER

(71) Applicant: Guangdong Aoyun Technology Co., Ltd., Huizhou (CN)

(72) Inventor: Xueping Zhu, Huizhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/680,265

(22) Filed: May 31, 2024

(65) Prior Publication Data

US 2025/0161104 A1 May 22, 2025

Related U.S. Application Data

(63) Continuation-in-part of application No. 18/514,327, filed on Nov. 20, 2023, now Pat. No. 12,115,099.

(51) Int. Cl.
*A61F 7/00* (2006.01)

(52) U.S. Cl.
CPC ...... *A61F 7/007* (2013.01); *A61F 2007/0036* (2013.01); *A61F 2007/0078* (2013.01); *A61F 2007/0087* (2013.01)

(58) Field of Classification Search
CPC .............. A61F 7/007; A61F 2007/0036; A61F 2007/0078; A61F 2007/0087; H01R 24/00; H05B 3/06; A61H 2205/065
See application file for complete search history.

(56) References Cited

U.S. PATENT DOCUMENTS

2012/0310120 A1* 12/2012 Orlando .................. A61H 1/00
601/15
2024/0350300 A1† 10/2024 Hu

FOREIGN PATENT DOCUMENTS

CN 204951305 U † 1/2016
CN 207949984 U † 10/2018
CN 210320254 † 4/2020
CN 210320254 U † 4/2020
CN 306791991 S † 8/2021
(Continued)

OTHER PUBLICATIONS

"Definition of Suction," Merriam-webster.com. [Online]. Available: https://www.merriam-webster.com/dictionary/suction. (Year: 2024).*
(Continued)

*Primary Examiner* — Joanne M Rodden
*Assistant Examiner* — Dana Stumpfoll

(57) ABSTRACT

A combined hand warmer includes a first hand warmer unit and a second hand warmer unit. The first hand warmer unit is provided with the first connecting portion. The second hand warmer unit is provided with the second connecting portion. The first connecting portion and the second connecting portion are detachably connected, so that the first hand warmer unit and the second hand warmer unit are combined into a whole. When a user needs to use the hand warmer to simultaneously warm the hands/multiple body parts, the first hand warmer unit can be separated from the second hand warmer unit. When a user only needs to use the hand warmer to warm one hand/one body part, the first connecting portion can be connected to the second connecting portion to combine the first hand warmer unit with the second hand warmer unit into a whole.

9 Claims, 16 Drawing Sheets

(56) References Cited

FOREIGN PATENT DOCUMENTS

| | | | | |
|---|---|---|---|---|
| CN | 307668019 | S | † | 11/2022 |
| CN | 220193313 | U | † | 6/2023 |
| CN | 308088488 | S | † | 6/2023 |
| CN | 219847034 | | † | 10/2023 |
| CN | 219847034 | U | † | 10/2023 |
| CN | 219940987 | U | † | 11/2023 |
| CN | 220193313 | | † | 12/2023 |
| KR | 20160001001 | U | * | 9/2014 |
| KR | 101989309 | B1 | * | 11/2018 |

OTHER PUBLICATIONS

"Ocoopa hand warmers rechargeable 2 pack, magnetic electric handwarmer, 4 levels heat up to 136°F, USB-C portable charger 10000mAh, raynauds, golf, tech gifts for men, UT2s(MagTwins)," Jul. 29, 2022. Available: https://www.amazon.com/OCOOPA-Rechargeable-Magnetic-Electric-Handwarmer/dp/BOB7XR7PPD?th=1. (Year: 2022).*

"2 Pack Hand Warmer Rechargeable, Magnetic Twins Electric Hand Warmer, Reusable Type-C USB Handwarmer, Portable Hand Warmer 8000mAh, Great for Outdoor Sports, Hunting, Camping, Golf, Warm Gifts." Amazon.Com, Sep. 14, 2020, www.amazon.com/dp/B08HZ1ZRF2/ref=va_live_carousel?pf_rd_r=SC7SV053WS815WOZRG4J& (Year: 2020).*

B0CC19PD7L Publication datedJul. 15, 2023 Publisher: Shenzhen Street Cat Technology Co., Ltd Place of publication: amazon.com Link: https://www.amazon.com/OCOOPA-Rechargeable-Electric-Handwarmers-Certified/dp/B0CC19PD7L/ref=sr_1_6?crid=2TMP1DX6EUYGJ&dibeyJ2ljoiMSJ9.WFtyv-fTBxk7hCA9YWelzY5CcXc0cYhJI-DxSZgZ6pT4RoTOO3gc7RAFp9D42Bxfx8XgDLdhri3iqSGx9pur86qNMvu-0Z1kEHyFd6BzlUeeZMiAt1ycTTxGFy5NMpDY501dwd8FL_QwcDI_aouNtvsmLsm0VuaSA06980G4ljNfiaBPFwlwsGS4iwQAx6X72cSXtQVMRyWr7GIZI6lt_C3eAl8qtVkhOM-CLU9vd7EX2S1P6Jy8Jdmg8KM5RyC3vYvz5bseltqgpza291Np4SEWsw4ZhQvEwqoV62ZkbCQ.PLUjd--Vd_k9mZ63cpLUj-Fi2Laz64lj-4iqIMJPTE4&dibtag=se&keyword=hand%2Bwarmer%2BUT2S&qid1750132483&sprefixhand%2Bwarmer%2But2s%2Caps%2C352&sr8-6&th1.†

B0CBX155FP Publication dateSep. 4, 2023 Publisher: Shenzhen Street Cat Technology Co., Ltd Place of publication: amazon.com Link: https://www.amazon.com/OCOOPA-Rechargeable-Magnetic-Double-Sided-Electric/dp/B0CBX155FP/ref=sxin_16_pa_sp_search_thematic_sspa?content-id=amzn1.sym.2da95b6c-f59a-4699-bc43-doff036c6388%3Aamzn1.sym.2da95b6c-f59a-4699-bc43-doff036c6388&cridGBH223FWW6LA&cvct_cx=Rechargeable%2Bhand%2Bwarmer&keyword=Rechargeable%2Bhand%2Bwarmer&pdrd_i=BOCBX155FP&pdrd_r=ba2a82b2-b173-4f42-877b-bd9d9026a2d1&pdrd_w=HogIR&pdrd_wg=0V206&pfrd_p=2da95b6c-f59a-4699-bc43-doff036c6388&pfrd_r=JSSM3S797PS1WBVBC948&qid1750132594&refresh1&sboRZvfv%2F%2FHxDF%2BO5021pAnSA%3D%3D&sprefixrechargeable%2Bhand%2Bwarmer%2Caps%2C309&sr1-4-6024b2a3-78e4-4fed-8fed-e1613be3bcce-spons&spcsd=d2lkZ2V0TmFtZT1zcF9zZWFyY2hfdGhlbWF0aWM&th.†

B0B7XSMR2P Publication dateJul. 28, 2022 Publisher: Lifesystems Place of publication: amazon.com Link: https://www.amazon.co.uk/Lifesystems-Rechargeable-Twin-Pack-Dual-Palm-Functionality/dp/BOB7XSMR2P/ref=sr_1_35?crid=3TTVN94A5LL8W&dibeyJ2ljoiMSJ9.rKWt4_H-Ym_FfBqrYG7gP_w3emlyoWi1DJ8otxNxYlo1AuxMM1hHWa6tyf3edu7q-62At4SHHtK2LGVHOInQaCXVM-M5RWIYukt91hVZ24yqVshUTH0elB0P7ug-1KW7GhGUQQVQ1XDN2Q97QPmvrqLzzuaMDw3e8Xm6qyUUpbqkUdHe3uneaelin-wjIYXQSQVmFeR9AV5ubrln1vyonneAqjZ0TowGKGbaS6A04UHkG8tAPOARfqyAiWoq2Opi.SfYk26mpo4bDkG5yWHuRDISqe5AJldTSYZ2HWjhpcZo&dibtag=se&keyword=Rechargeable%2Bhand%2Bwarmer&qid1750132732&ssports&sprefixrechargeable%2Bhand%2Bwarmer%2Csports%2C352&sr1-35&xpidqp06mOv6iiN6l&th1.†

B0CJM27SKN Publication dateSep. 26, 2023 Publisher: Babacom Place of publication: amazon.com Link: https://www.amazon.co.uk/Babacom-Rechargeable-Reusable-Electric-Handwarmers/dp/BOCJM27SKN/ref=sr_1_56?crid=3TTVN94A5LL8W&dibeyJ2ljoiMSJ9.ER24by_T7Bajhe0medYrFKyzyw_KErDt2_dBW7KELjlrXIzNieMPLPP9Wni-dvs8OV42WapGX1S0IOk_VnibMOFIUN6OEc3qZobH0cc7Sk.TZEU-VjOQaEtamateM8UKsCuhw0N7U5ghcrMWh5nEtQ&dibtag=se&keyword=Rechargeable+hand+warmer&qid1750132817&ssports&sprefixrechargeable+hand+warmer%2Csports%2C352&sr1-56&xpidqp06mOv6iiN6l.†

B0CJGXZ5V1 Publication dateSep. 25, 2023 Publisher:Dongguan Hongyutai Electronic Co., Ltd Place of publication: amazon.com Link: Rechargeable-Split-Magnetic-Outdoor%EF%BC%88deep/dp/B0CJGXZ5V1/ref=sr_1_105?crid=3TTVN94A5LL8W&dibeyJ2ljoiMSJ9.ow0mx10CgLZBtMzMfx9lpWscYqBkJwf5AaUm8RuomuP6c3qXU8k7E1SnZvvtPkdLNwgWRCpOANXSoeU9Pwcgl-vsvnNplevVZcVEr2F0gvl.hjwAXEYMis8rz-yjA7CMQ3J6uis4aWrkWPzqlcRbeas&dibtag=se&keyword=Rechargeable%2Bhand%2Bwarmer&qid1750132872&ssports&sprefixrechargeable%2Bhand%2Bwarmer%2Csports%2C352&sr1-105&xpidqp06mOv6iiN6l&th1.†

ASIN: B0BK8YX8DR Title: Hand Warmers Rechargeable: 2 in 1 Magnetic Electric Hand Warmer 10000mAh, Warm 15 Hours Portable Reusable Power Bank Hand Warmers, 3 Levels, Great Gift for Outdoor Sports, Camping UCL: https://www.amazon.com/dp/B0BK8YX8DR Date First Available: Oct. 24, 2022.†

ASIN: B0CJRGM51P Title: Hand Warmers Rechargeable 2 Pack, Rechargeable Hand Warmer, Pocket Portable Electric Hand Warmer, Reusable Handwarmers, A Winter Christmas Hand-Warming Gift for Work, Camping, Golf, and Hunting UCL: https://www.amazon.com/dp/B0CJRGM51P Date First Available: Aug. 31, 2023.†

* cited by examiner
† cited by third party

COMBINED TYPE HAND WARMER

CROSS-REFERENCE TO RELATED APPLICATIONS

This application is a Continuation-in-Part of the U.S. application Ser. No. 18/514,327 filed on Nov. 20, 2023, and entitled "COMBINED TYPE HAND WARMER," now pending, the entire disclosures of which are incorporated herein by reference.

TECHNICAL FIELD

The present disclosure relates to the field of hand warmers, and particularly, to a combined hand warmer.

BACKGROUND

Whether it is double-sided or single-sided, existing hand warmers on the market are usually only able to warm one hand/one body part, making it difficult to simultaneously warm both hands/multiple body parts. Especially when a user needs to perform different actions with the hands separately or when a user intends to use the hand warmer to warm multiple body parts, it is hard for the current hand warmers to meet the need of the user. Therefore, there is an urgent need on the market to provide a hand warmer that can be used to warm the two hands/multiple body parts simultaneously and is convenient for users to carry.

SUMMARY

In order to overcome the shortcomings of the prior art, the present disclosure provides a hand warmer that can be used to warm the two hands/multiple body parts simultaneously and is convenient for users to carry.

The technical solution adopted by the present disclosure to solve the technical problem is as follows.

A combined hand warmer includes a first hand warmer unit and a second hand warmer unit, wherein the first hand warmer unit includes a first outer surface and a first connecting inner surface opposite to the first outer surface; the second hand warmer unit includes a second outer surface and a second connecting inner surface opposite to the second outer surface; the first connecting inner surface includes a first connecting portion; the second connecting inner surface includes a second connecting portion; and the first connecting portion and the second connecting portion are magnetically connected to each other through a buckle or a plurality of magnetic suction components; and to connect the first connecting inner surface to the second connecting inner surface, the first hand warmer unit and the second hand warmer unit are combined into a whole.

As an improvement of the present disclosure, the first connecting portion is connected to the second connecting portion through a buckle; the first connecting portion includes a first buckle portion; the second connecting portion includes a first buckle fitting portion; and the first buckle portion is detachably connected to the first buckle fitting portion, so that the first connecting inner surface is buckled to the second connecting inner surface, and the first hand warmer unit and the second hand warmer unit are combined into a whole.

As an improvement of the present disclosure, the first connecting portion further includes a second buckle portion; the second connecting portion further includes a second buckle fitting portion; and when the first buckle portion is detachably plugged into the first buckle fitting portion, the second buckle portion is detachably plugged into the second buckle fitting portion.

As an improvement of the present disclosure, the first buckle portion is a buckle or a buckle slot, and the first buckle fitting portion is a buckle slot or a buckle; when the first buckle portion is a buckle, the first buckle fitting portion is a buckle slot; when the first buckle portion is a buckle slot, the first buckle fitting portion is a buckle; the second buckle portion is a buckle or a buckle slot, and the second buckle fitting portion is a buckle slot or a buckle; when the second buckle portion is a buckle, the second buckle fitting portion is a buckle slot; and when the second buckle portion is a buckle slot, the second buckle fitting portion is a buckle.

As an improvement of the present disclosure, the first buckle portion is a first buckle, the first buckle fitting portion is a first buckle slot, and the first buckle is detachably plugged into the first buckle slot.

As an improvement of the present disclosure, the second buckle portion is a second buckle slot, and the second buckle fitting portion is a first buckle; and when the first buckle is detachably plugged into the first buckle slot, the second buckle is detachably plugged into the second buckle slot.

As an improvement of the present disclosure, the first connecting portion further includes a first positioning column, and the second connecting portion further includes a first positioning hole; and when the first positioning column is located in the first positioning hole, the first buckle is detachably plugged into the first buckle slot, and the second buckle is detachably plugged into the second buckle slot.

As an improvement of the present disclosure, the first connecting portion further includes a second positioning hole, and the second connecting portion further includes a second positioning column; and when the first positioning column is located in the first positioning hole and the second positioning column is located in the second positioning hole, the first buckle is detachably plugged into the first buckle slot, and the second buckle is detachably plugged into the second buckle slot.

As an improvement of the present disclosure, the first connecting portion further includes a first guide slot; the first positioning column is located on an upper side of the first guide slot; the second positioning hole is located on a lower side of the first guide slot; the second connecting portion further includes a second guide slot; the first positioning hole is located on an upper side of the first guide slot; the second positioning column is located on a lower side of the first guide slot; and when the first positioning column slides into the first positioning hole along the second guide slot, and the second positioning column slides into the second positioning hole along the first guide slot, the first buckle is detachably plugged into the first buckle slot, and the second buckle is detachably plugged into the second buckle slot.

As an improvement of the present disclosure, the first buckle is arranged on one side of the first hand warmer unit, and the second buckle slot is arranged on the other side of the first hand warmer unit in a manner of being symmetric to the first buckle; and the second buckle is arranged on one side of the second hand warmer unit, and the first buckle slot is arranged on the other side of the second hand warmer unit in a manner of being symmetric to the second buckle.

As an improvement of the present disclosure, a first charging port is further arranged on the first outer surface of the first hand warmer unit; the first charging port is configured to charge the first hand warmer unit; a second charging port is further arranged on the second outer surface of the second hand warmer unit; and the second charging port is configured to charge the second hand warmer unit.

As an improvement of the present disclosure, the first buckle portion is a spinning buckle; the first buckle fitting portion is a spinning slot; and the spinning buckle is detachably connected to the spinning slot.

As an improvement of the present disclosure, a stop convex block is arranged on the spinning buckle; a stop edge is arranged on the spinning slot; a notch is arranged on the stop edge; the notch is connected to the spinning slot; when the stop convex block rotates with the spinning buckle to the notch, the stop convex block is placed into the spinning slot along with the spinning buckle via the notch; and when stop convex block is placed into the spinning slot along with the spinning buckle via the notch, the spinning buckle is rotated to enable the stop convex block to rotate to be staggered from the notch, so that the stop edge stops the stop convex block of the spinning buckle in the spinning slot, and the first hand warmer unit and the second hand warmer unit are combined into a whole.

As an improvement of the present disclosure, the first hand warmer unit is further provided with a first power indicator lamp; the first power indicator lamp is configured to display a battery level of the first hand warmer unit; the second hand warmer unit is further provided with a second power indicator lamp; the second power indicator lamp is configured to display a battery level of the second hand warmer unit; the first hand warmer unit is further provided with a first ON/OFF button; the first ON/OFF button is configured to control on and off of the first hand warmer unit; the second hand warmer unit is further provided with a second ON/OFF button; and the second ON/OFF button is configured to control on and off of the second hand warmer unit.

As an improvement of the present disclosure, wherein the first connecting portion and the second connecting portion are magnetically connected through a plurality of magnetic suction components; the first connecting portion includes a first magnetic suction member; the second connecting portion includes a first magnetic suction fitting piece; the first magnetic suction member and the first magnetic suction fitting piece are mutually sucked, so that the first connecting inner surface is sucked on the second connecting inner surface; and the first hand warmer unit and the second hand warmer unit are combined into a whole.

As an improvement of the present disclosure, wherein the first connecting portion further includes a second magnetic suction fitting piece; the second connecting portion further includes a second magnetic suction member; the second magnetic suction fitting piece and the second magnetic suction member are mutually sucked to suck the first connecting inner surface onto the second connecting inner surface; and the first hand warmer unit and the second hand warmer unit are combined into a whole.

As an improvement of the present disclosure, the first connecting portion includes a third magnetic suction member; the second connecting portion includes a third magnetic suction fitting piece; the third magnetic suction member and the third magnetic suction fitting piece are mutually sucked, so that the first connecting inner surface is sucked to the second connecting inner surface, and the first hand warmer unit and the second hand warmer unit are combined into a whole; the first connecting portion further includes a fourth magnetic suction fitting piece, and the second connecting portion further includes a fourth magnetic suction member; and the fourth magnetic suction fitting piece and the fourth magnetic suction member are mutually sucked, so that the first connecting inner surface is sucked to the second connecting inner surface, and the first hand warmer unit and the second hand warmer unit are combined into a whole.

As an improvement of the present disclosure, the first connecting inner surface further includes a first mounting hole; the second connecting inner surface includes a second mounting hole; the first magnetic suction member is arranged in the first mounting hole; the first magnetic suction fitting piece is arranged in the second mounting hole; or, the first magnetic suction member is connected to the first connecting inner surface through an adhesive; and the first magnetic suction fitting piece is connected to the second connecting inner surface through an adhesive.

As an improvement of the present disclosure, the first magnetic suction member is circular or elliptical; a length range of the first magnetic suction member is 5-25 mm; a width range of the first magnetic suction member is 5-25 mm; the first magnetic suction fitting piece is circular or elliptical; a length range of the first magnetic suction fitting piece is 5-25 mm; a width range of the first magnetic suction fitting piece is 5-25 mm; or, the first magnetic suction member is elongated; a length range of the first magnetic suction member is 10-30 mm; a width range of the first magnetic suction member is 3-10 mm; the first magnetic suction fitting piece is elongated; a length range of the first magnetic suction fitting piece is 10-30 mm; and a width range of the first magnetic suction fitting piece is 3-10 mm.

As an improvement of the present disclosure, an area of the first magnetic suction member accounts for 5%-20% of an area of the first connecting inner surface, and an area of the first magnetic suction fitting piece accounts for 5%-20% of an area of the second connecting inner surface.

The present disclosure has the beneficial effects: The present disclosure provides a combined hand warmer. Due to the first hand warmer unit and the second hand warmer unit, the first hand warmer unit is provided with the first connecting portion, and the second hand warmer unit is provided with the second connecting portion; the first connecting portion and the second connecting portion are detachably connected, so that the first hand warmer unit and the second hand warmer unit are combined into a whole. When a user needs to use the hand warmer to simultaneously warm the hands/multiple body parts, the first hand warmer unit can be separated from the second hand warmer unit, so that the first hand warmer unit and the second hand warmer unit can be used for warming the two hands/multiple different body parts respectively. When a user only needs to use the hand warmer to warm one hand/one body part, the first connecting portion can be connected to the second connecting portion to combine the first hand warmer unit with the second hand warmer unit into a whole, so as to enlarge a warming area of the hand warmer for one hand/one body part and improve the warming effect. Furthermore, when a user needs to carry or store the hand warmer, the user can select to separately carry and store the first hand warmer and the second hand warmer according to an actual situation, or select to combine the first hand warmer with the second hand warmer into a whole to satisfy the use in multiple scenarios by a user, which greatly improves the user experience.

BRIEF DESCRIPTION OF THE DRAWINGS

In order to explain the technical solutions of the embodiments of the present disclosure more clearly, the following will briefly introduce the accompanying drawings used in the embodiments. The drawings in the following description are only some embodiments of the present disclosure. Those of ordinary skill in the art can obtain other drawings based on these drawings without creative work.

The present disclosure is further described below in detail in combination with the accompanying drawings and embodiments.

DETAILED DESCRIPTION OF THE EMBODIMENTS

Figure 1:
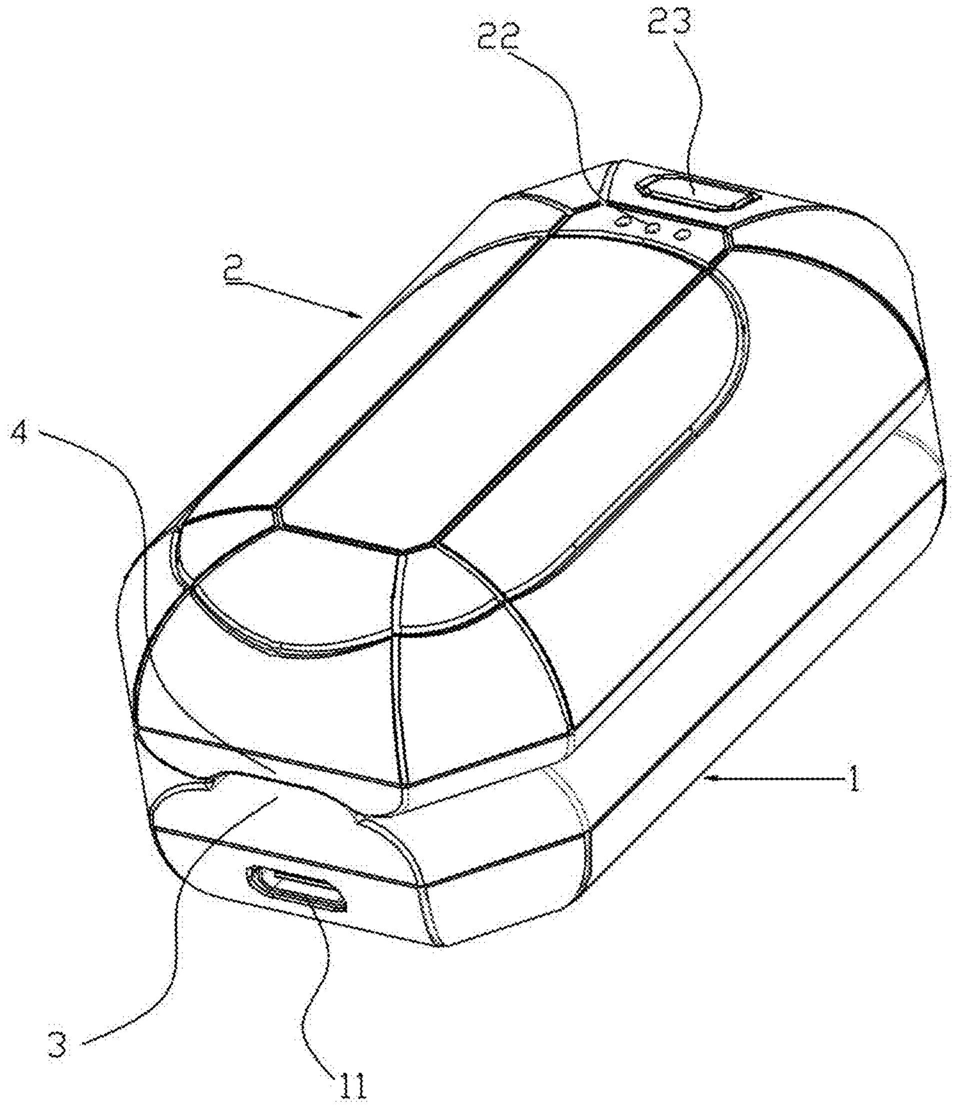
FIG. 1 is a schematic diagram of an entire structure of the present disclosure.
Figure 2:
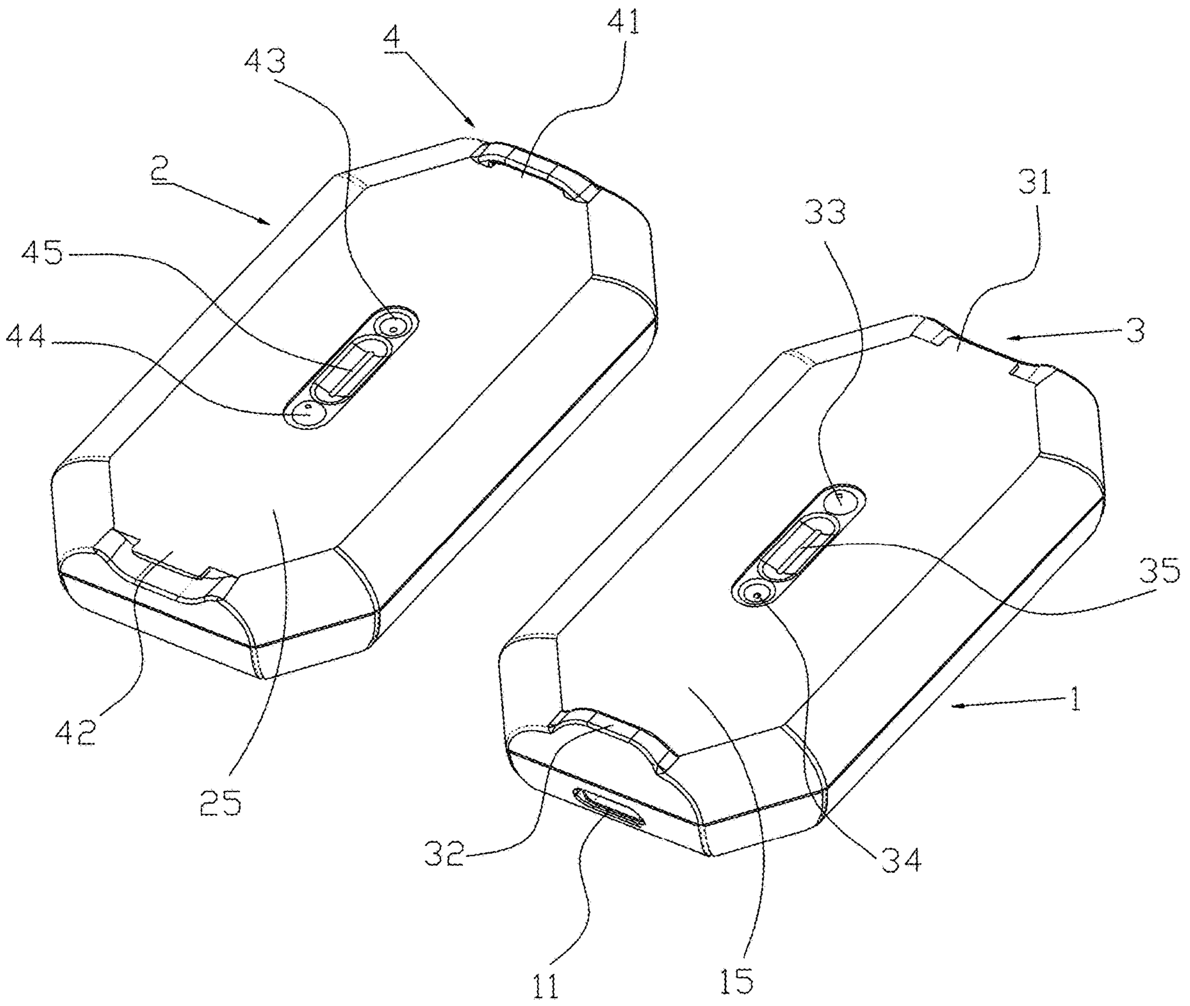
FIG. 2 is an exploded view of the present disclosure.
Figure 3:
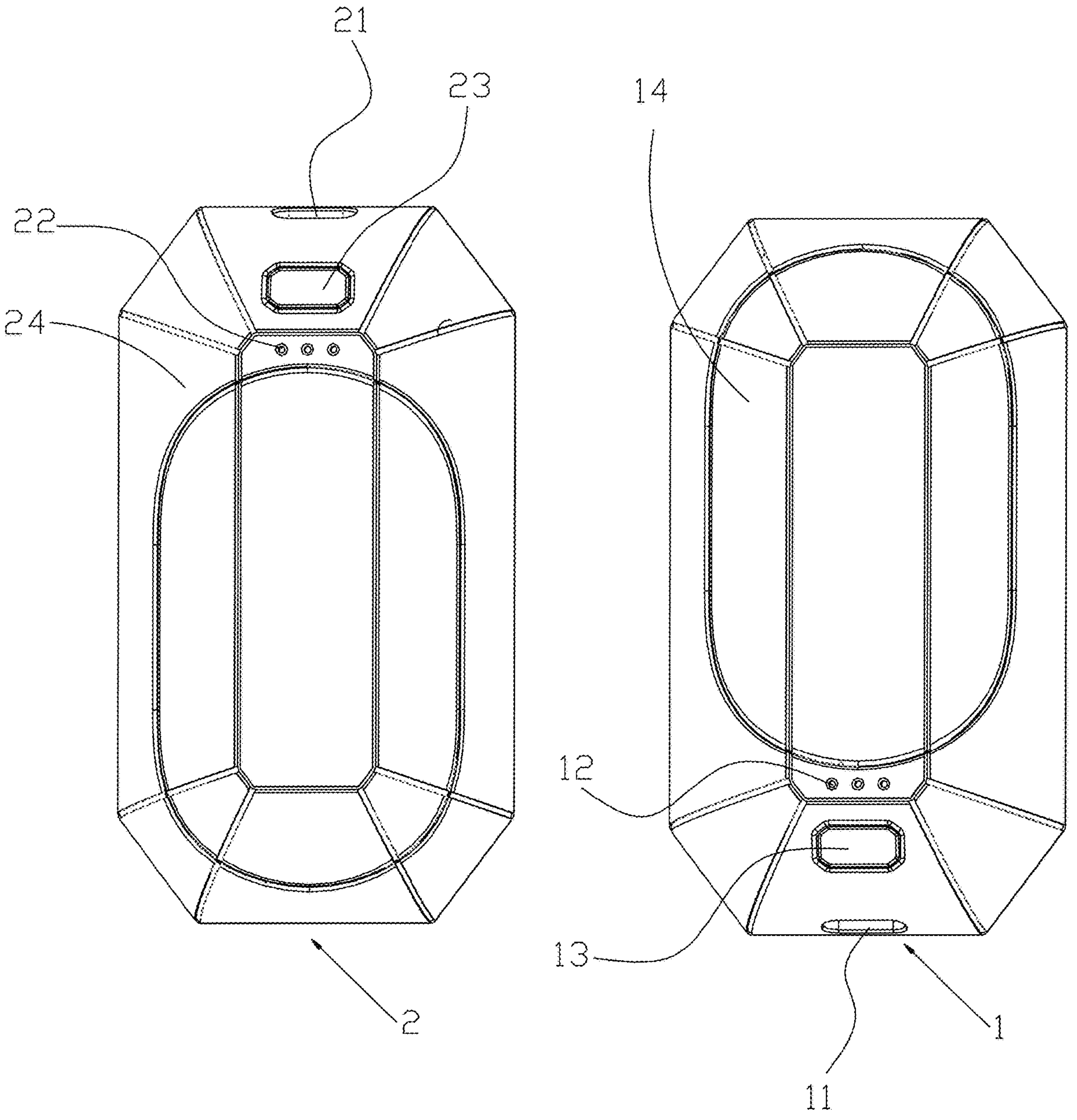
FIG. 3 is another exploded view of the present disclosure.
Figure 4:
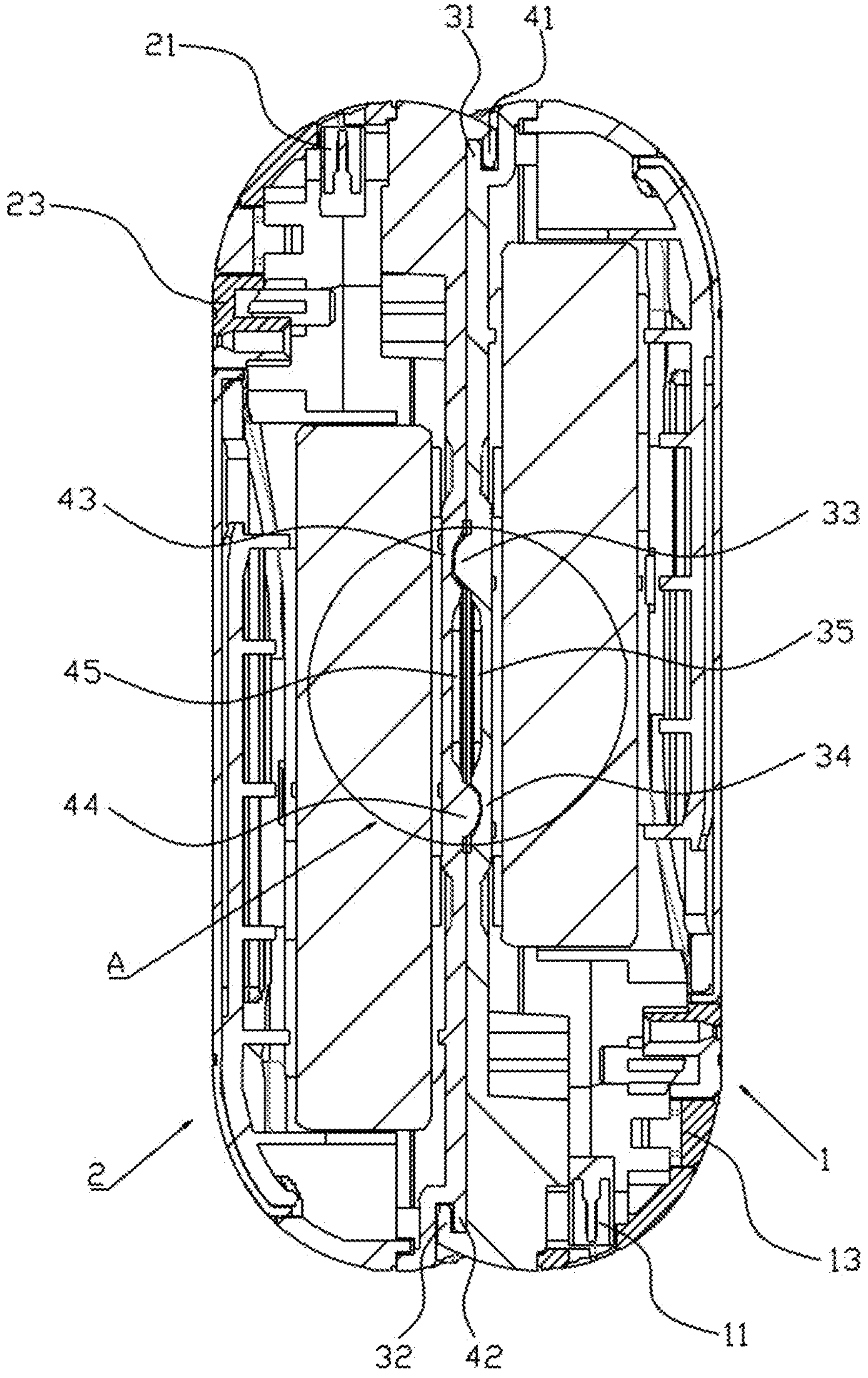
FIG. 4 is a sectional view cut away along a first connecting portion and a second connecting portion.
Figure 5:
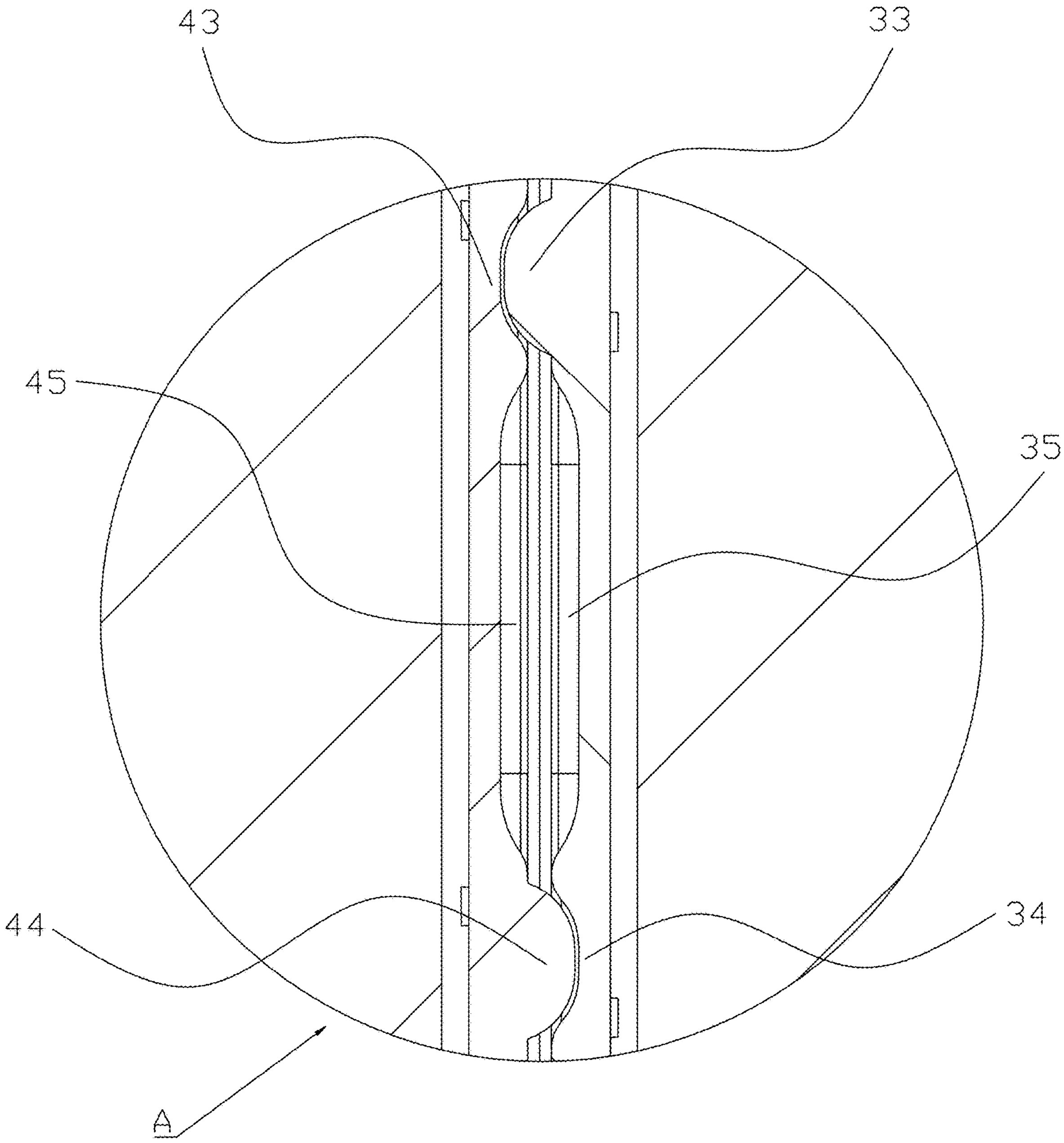
FIG. 5 is an enlarged view of the part A in FIG. 4.

Referring to FIG. 1 to FIG. 5, a combined hand warmer includes a first hand warmer unit 1 and a second hand warmer unit 2, wherein the first hand warmer unit 1 is provided with a first connecting portion 3; the second hand warmer unit 2 is provided with a second connecting portion 4; the first connecting portion 3 is detachably connected to the second connecting portion 4, so that the first hand warmer unit 1 and the second hand warmer unit 2 are combined into a whole. Through the above structure, due to the first hand warmer unit and the second hand warmer unit, the first hand warmer unit is provided with the first connecting portion, and the second hand warmer unit is provided with the second connecting portion; the first connecting portion and the second connecting portion are detachably connected, so that the first hand warmer unit and the second hand warmer unit are combined into a whole. When a user needs to use the hand warmer to simultaneously warm the hands/multiple body parts, the first hand warmer unit can be separated from the second hand warmer unit, so that the first hand warmer unit and the second hand warmer unit can be used for warming the two hands/multiple different body parts respectively. When a user only needs to use the hand warmer to warm one hand/one body part, the first connecting portion can be connected to the second connecting portion to combine the first hand warmer unit with the second hand warmer unit into a whole, so as to enlarge a warming area of the hand warmer for one hand/one body part and improve the warming effect. Furthermore, when a user needs to carry or store the hand warmer, the user can select to separately carry and store the first hand warmer and the second hand warmer according to an actual situation, or select to combine the first hand warmer with the second hand warmer into a whole to satisfy the use in multiple scenarios by a user, which greatly improves the user experience.

In this embodiment, the first hand warmer unit includes a first outer surface 14 and a first connecting inner surface 15 opposite to the first outer surface 14; the second hand warmer unit includes a second outer surface 24 and a second connecting inner surface 25 opposite to the second outer surface 24; the first connecting inner surface 15 includes a first connecting portion 3; the second connecting inner surface 25 includes a second connecting portion 4; the first connecting portion 3 includes a first buckle portion; the second connecting portion 4 includes a first buckle fitting portion; the first buckle portion is detachably connected to the first buckle fitting portion, so that the first connecting inner surface 15 is buckled to the second connecting inner surface 25, and the first hand warmer unit 1 and the second hand warmer unit 2 are combined into a whole.

The first connecting portion 3 is connected to the second connecting portion 4 through a buckle or magnetic suction, so that the first connecting inner surface 15 is connected to the second connecting inner surface 25, and the first hand warmer unit 1 and the second hand warmer unit 2 are combined into a whole.

Specifically, referring to FIG. 1 to FIG. 5, in some embodiments, the first connecting portion 3 is connected to the second connecting portion 4 through a buckle. The first connecting portion 3 further includes a second buckle portion; the second connecting portion 4 further includes a second buckle fitting portion. When the first buckle portion is detachably plugged into the first buckle fitting portion, the second buckle portion is detachably plugged into the second buckle fitting portion.

Specifically, the first buckle portion is a buckle or a buckle slot, and the first buckle fitting portion is a buckle slot or a buckle; when the first buckle portion is a buckle, the first buckle fitting portion is a buckle slot; when the first buckle portion is a buckle slot, the first buckle fitting portion is a buckle; the second buckle portion is a buckle or a buckle slot, and the second buckle fitting portion is a buckle slot or a buckle; when the second buckle portion is a buckle, the second buckle fitting portion is a buckle slot; and when the second buckle portion is a buckle slot, the second buckle fitting portion is a buckle.

In this embodiment, the first buckle portion is a first buckle 31, the first buckle fitting portion is a first buckle slot 41, and the first buckle 31 is detachably plugged into the first buckle slot 41. The second buckle portion is a second buckle slot 32, and the second buckle fitting portion is a second buckle 42. When the first buckle 31 is detachably plugged into the first buckle slot 41, the second buckle 42 is detachably plugged into the second buckle slot 32. Through the above structure, the structure is simple, the connection is stable, and the detachable connection between the first connecting portion and the second connecting portion is effectively achieved. Moreover, in this embodiment, the detachable connection between the first connecting portion and the second connecting portion can be further achieved by using a detachable connection mode such as male and female snappers and male and female hook and loop fasteners.

In this embodiment, the first connecting portion 3 further includes a first positioning column 33, and the second connecting portion 4 further includes a first positioning hole 43; and when the first positioning column 33 is located in the first positioning hole 43, the first buckle 31 is detachably plugged into the first buckle slot 41, and the second buckle 42 is detachably plugged into the second buckle slot 32. The first connecting portion 3 further includes a second positioning hole 34, and the second connecting portion 4 further includes a second positioning column 44; and when the first positioning column 33 is located in the first positioning hole 43 and the second positioning column 44 is located in the second positioning hole 34, the first buckle 31 is detachably plugged into the first buckle slot 41, and the second buckle 42 is detachably plugged into the second buckle slot 32. Specifically, the first connecting portion 3 further includes a first guide slot 35; the first positioning column 33 is located on an upper side of the first guide slot 35; the second positioning hole 34 is located on a lower side of the first guide slot 35; the second connecting portion 4 further includes a second guide slot 45; the first positioning hole 43 is located on an upper side of the first guide slot 45; the second positioning column 44 is located on a lower side of the first guide slot 45; and when the first positioning column 33 slides into the first positioning hole 43 along the second guide slot 45, and the second positioning column 44 slides into the second positioning hole 34 along the first guide slot 35, the first buckle 31 is detachably plugged into the first buckle slot 41, and the second buckle 42 is detachably plugged into the second buckle slot 32. Further, the first buckle 31 is arranged on one side of the first hand warmer unit 1, and the second buckle slot 32 is arranged on the other side of the first hand warmer unit 1 in a manner of being symmetric to the first buckle; and the second buckle 42 is arranged on one side of the second hand warmer unit 2, and the first buckle slot 41 is arranged on the other side of the second hand warmer unit 2 in a manner of being symmetric to the second buckle. Through the above structure, by the connection between the first positioning column and the first positioning hole, and the connection between the seconds positioning column and the second positioning hole, it can ensure that the first buckle is fully plugged into the first buckle slot, and the second buckle is fully plugged into the second buckle slot, so as to improve the stability of connection between the first hand warmer unit and the second hand warmer units. Furthermore, through the first guide slot, it can ensure that the second positioning column slides quickly and accurately into the second positioning hole. Through the second guide slot, it can ensure that the first positioning column slides quickly and accurately into the first positioning hole, so as to quickly and accurately plug the first buckle into the first buckle slot, plug the second buckle into the second buckle slot, and complete the connection between the first hand warmer unit and the second hand warmer unit, so that the first hand warmer unit and the second hand warmer unit are combined into a whole. Further, as the first positioning column is located in the first positioning hole and the second positioning column is located in the second positioning hole, the first positioning column can be prevented from sliding out of the first positioning hole, and the second positioning column can be prevented from sliding out of the second positioning hole, thus preventing relative sliding between the first hand warmer unit and the second hand warmer unit and preventing the first hand warmer unit from being separated from the second hand warmer unit. Further, when a user needs to separate the first hand warmer unit from the second hand warmer unit, the user only needs to slide the first positioning column out of the first positioning hole, slide the second positioning column out of the second positioning hole, then slide the first buckle out of the first buckle slot, and slide the second buckle out of the second buckle slot, so as to complete the disassembling of the first hand warmer unit and the second hand warmer unit. This facilitates the user to use the first hand warmer unit and the second hand warmer unit to warm multiple body parts. The first hand warmer unit and the second hand warmer unit can even be used separately by different people. Meanwhile, it is also convenient for a user to separately carry and store the first hand warmer unit and the second hand warmer unit. Particularly, a user can carry the first hand warmer unit and the second hand warmer unit separately by putting them into pockets.

In this embodiment, a first charging port 11 is further arranged on the first outer surface 14 of the first hand warmer unit 1; the first charging port 11 is configured to charge the first hand warmer unit 1; a second charging port 21 is further arranged on the second outer surface 24 of the second hand warmer unit 2; and the second charging port 21 is configured to charge the second hand warmer unit 2. The first hand warmer unit 1 is further provided with a first power indicator lamp 12; the first power indicator lamp 12 is configured to display a battery level of the first hand warmer unit 1; the second hand warmer unit 2 is further provided with a second power indicator lamp 22; and the second power indicator lamp 22 is configured to display a battery level of the second hand warmer unit 2. Specifically, the first hand warmer unit 1 is further provided with a first ON/OFF button 13; the first ON/OFF button 13 is configured to control on and off of the first hand warmer unit 1; the second hand warmer unit 2 is further provided with a second ON/OFF button 23; and the second ON/OFF button 23 is configured to control on and off of the second hand warmer unit 2. Through the above structure, a user can charge the first hand warmer unit through the first charging port, charge the second hand warmer unit through the second charging port, observe a state of charge of the first hand warmer unit through the first power indicator lamp, and observe a state of charge of the second hand warmer unit through the second power indicator lamp. Further, a user can further select to power on or power off the first hand warmer unit through the first ON/OFF button, and power on or power off the second hand warmer unit through the second ON/OFF button.

Figure 6:
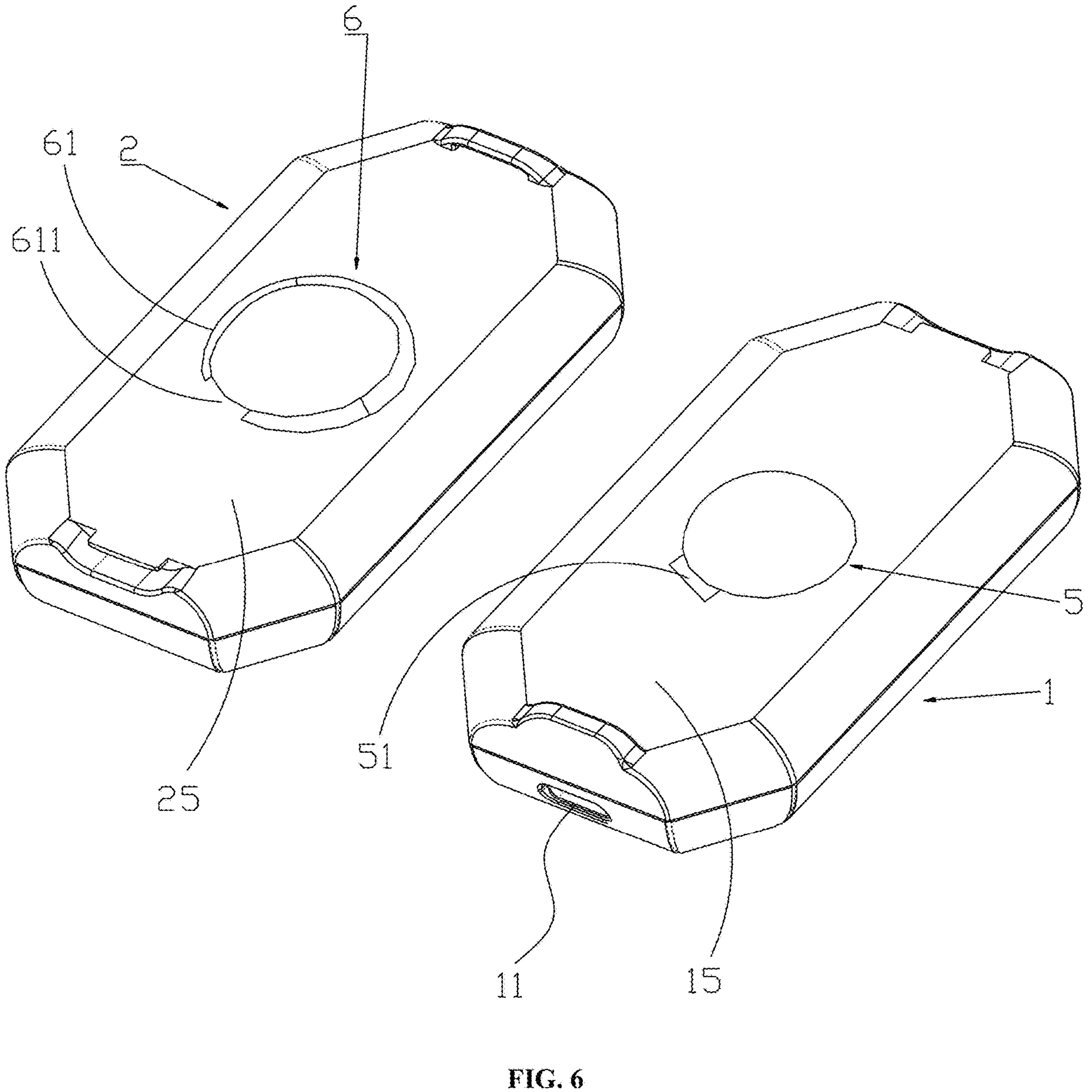
FIG. 6 is a schematic structural diagram of a spinning slot and a spinning buckle.
Figure 7:
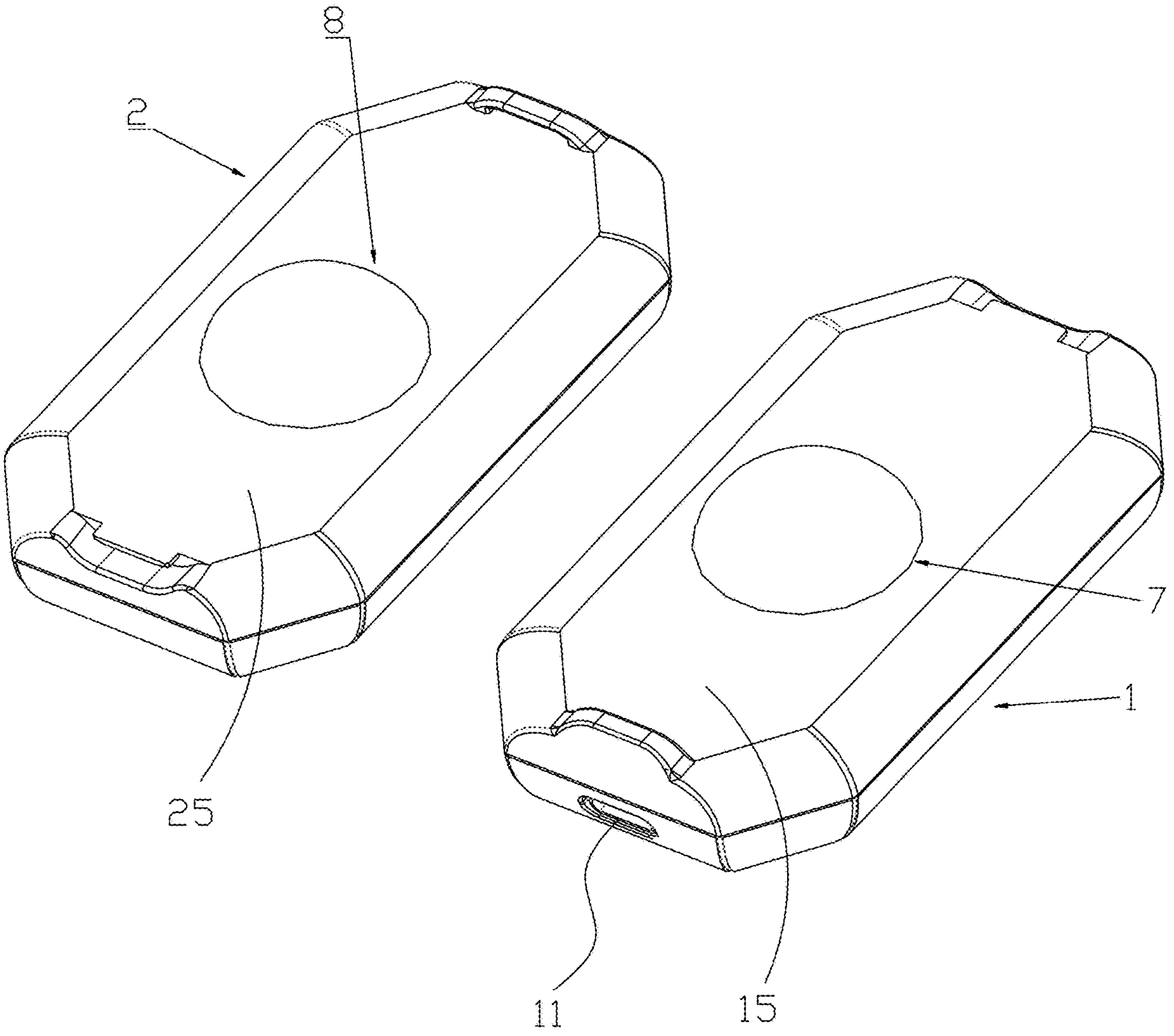
FIG. 7 is a schematic structural diagram of a first magnetic suction member and a first magnetic suction fitting piece.
Figure 15:
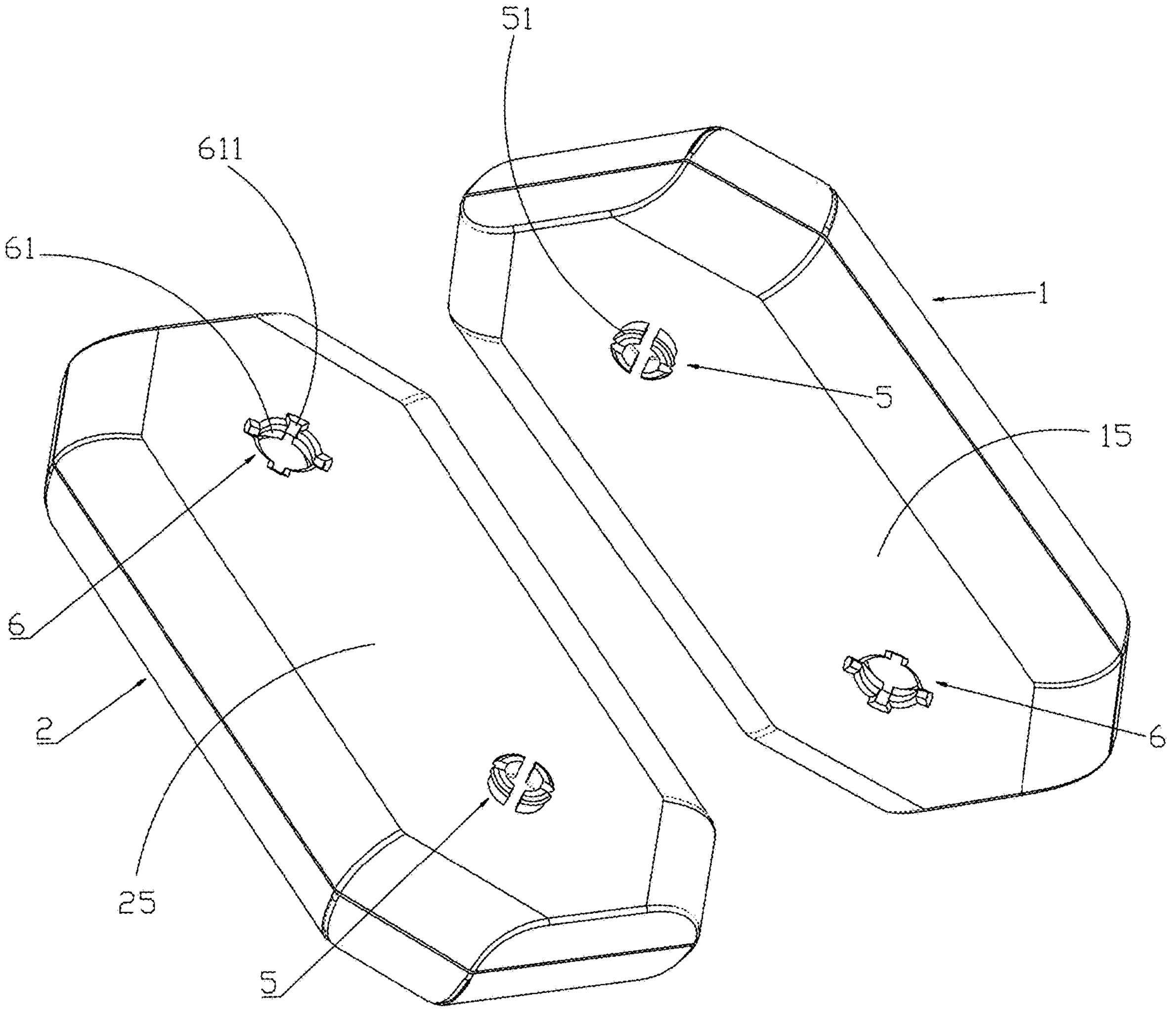
FIG. 15 is another schematic structural diagram of a spinning slot and a spinning buckle.
Figure 16:
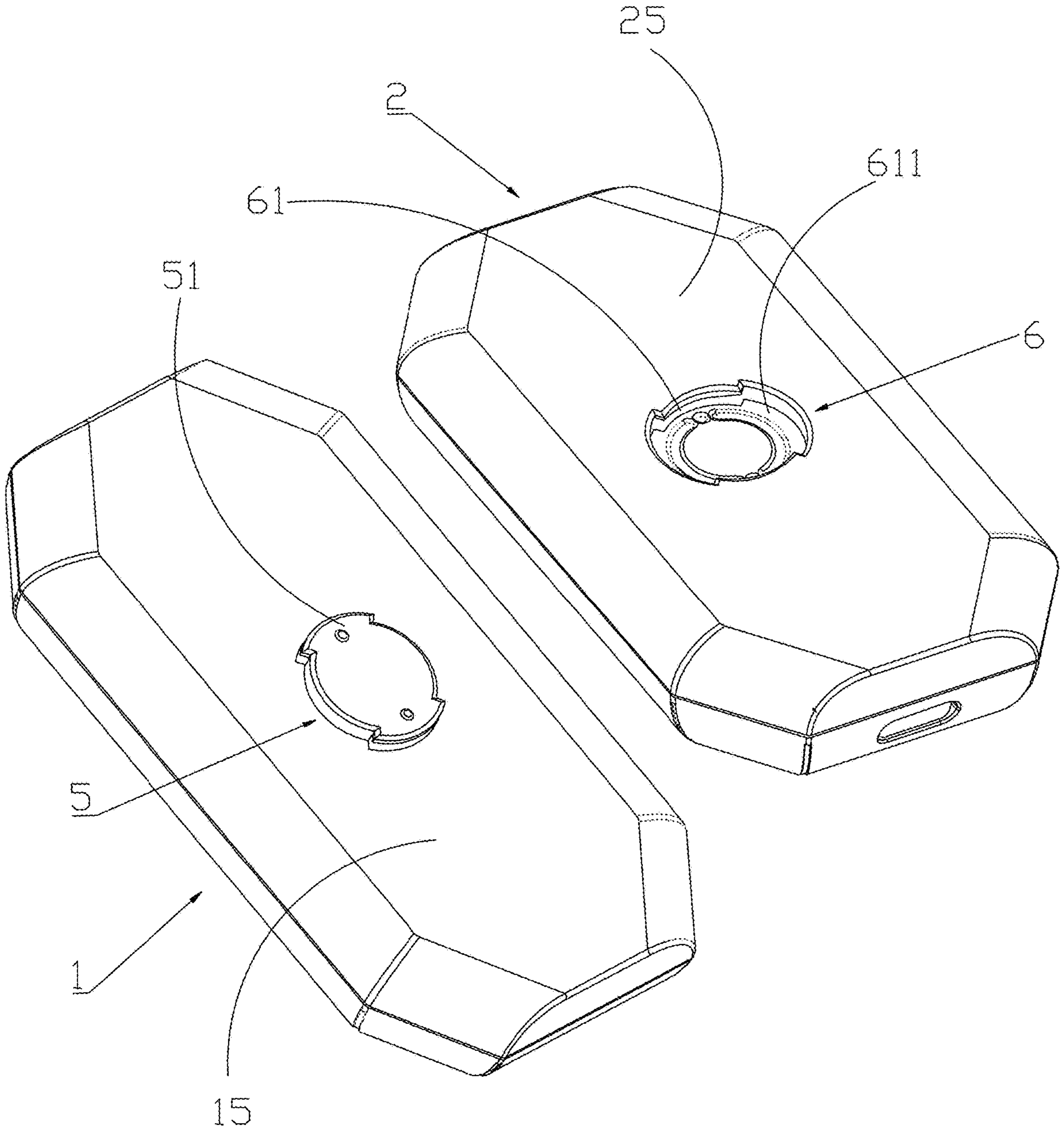
FIG. 16 is still another schematic structural diagram of a spinning slot and a spinning buckle.

Referring to FIG. 6, FIG. 15, and FIG. 16, in some embodiments, the first buckle portion is a spinning buckle 5; the first buckle fitting portion is a spinning slot 6; and the spinning buckle 5 is detachably connected to the spinning slot 6. A stop convex block 51 is arranged on the spinning buckle 5; a stop edge 61 is arranged on the spinning slot 6; a notch 611 is arranged on the stop edge 61; the notch 611 is connected to the spinning slot 6; when the stop convex block 51 rotates with the spinning buckle 5 to the notch 611, the stop convex block 51 can be placed into the spinning slot 6 along with the spinning buckle 5 via the notch 611; and when stop convex block 51 is placed into the spinning slot 6 along with the spinning buckle 5 via the notch 611, the spinning buckle 5 is rotated to enable the stop convex block 51 to rotate to be staggered from the notch 611, so that the stop edge 61 stops the stop convex block 51 of the spinning buckle 5 in the spinning slot 6, and the first hand warmer unit 1 and the second hand warmer unit 2 are combined into a whole.

Referring to FIG. 7 to FIG. 14, in some embodiments, the first connecting portion 3 and the second connecting portion 4 are magnetically connected; the first connecting portion 3 includes a first magnetic suction member 7; the second connecting portion 4 includes a first magnetic suction fitting piece 8; the first magnetic suction member 7 and the first magnetic suction fitting piece 8 are mutually sucked, so that the first connecting inner surface 15 is sucked on the second connecting inner surface 25; and the first hand warmer unit 1 and the second hand warmer unit 2 are combined into a whole. The first connecting portion 3 further includes a second magnetic suction fitting piece 71; the second connecting portion 4 further includes a second magnetic suction member 81; the second magnetic suction fitting piece 71 and the second magnetic suction member 81 are mutually sucked to suck the first connecting inner surface 15 onto the second connecting inner surface 25; and the first hand warmer unit 1 and the second hand warmer unit 2 are combined into a whole. Specifically, the first connecting portion 3 includes a third magnetic suction member 72; the second connecting portion 4 includes a third magnetic suction fitting piece 82; the third magnetic suction member 72 and the third magnetic suction fitting piece 82 are mutually sucked, so that the first connecting inner surface 15 is sucked to the second connecting inner surface 25, and the first hand warmer unit 1 and the second hand warmer unit 2 are combined into a whole; the first connecting portion 3 further includes a fourth magnetic suction fitting piece 73, and the second connecting portion 4 further includes a fourth magnetic suction member 83; and the fourth magnetic suction fitting piece 73 and the fourth magnetic suction member 83 are mutually sucked, so that the first connecting inner surface 15 is sucked to the second connecting inner surface 25, and the first hand warmer unit 1 and the second hand warmer unit 2 are combined into a whole.

Specifically, the first connecting portion 3 includes a third magnetic suction member 72; the second connecting portion 4 includes a third magnetic suction fitting piece 82; the third magnetic suction member 72 and the third magnetic suction fitting piece 82 are mutually sucked, so that the first connecting inner surface 15 is sucked to the second connecting inner surface 25, and the first hand warmer unit 1 and the second hand warmer unit 2 are combined into a whole; the first connecting portion 3 further includes a fourth magnetic suction fitting piece 73, and the second connecting portion 4 further includes a fourth magnetic suction member 83; and the fourth magnetic suction fitting piece 73 and the fourth magnetic suction member 83 are mutually sucked, so that the first connecting inner surface 15 is sucked to the second connecting inner surface 25, and the first hand warmer unit 1 and the second hand warmer unit 2 are combined into a whole. In addition, the first hand warmer unit 1 includes a first shell 38 and a second shell 39 assembled to the first shell 38, the second hand warmer unit 2 includes a third shell 48 and a fourth shell 49 assembled to the third shell 48, the first outer surface 14 is formed on an outer surface of the first shell 38, the first connecting inner surface 15 is formed on an outer surface of the second shell 39. Further, the first connecting inner surface 15 defines a first mounting hole 74; the second connecting inner surface 25 defines a second mounting hole 84; the first magnetic suction member 7 is arranged in the first mounting hole 74; the second outer surface 24 is formed on an outer surface of the fourth shell 49, the second connecting inner surface 25 is formed on an outer surface of the third shell 48, the first magnetic suction fitting piece 8 is arranged in the second mounting hole 84; or, the first magnetic suction member is connected to the first connecting inner surface 15 through an adhesive; and the first magnetic suction fitting piece is connected to the second connecting inner surface 25 through an adhesive. The first magnetic suction member, the second magnetic suction member, the third magnetic suction member, and the fourth magnetic suction member can be magnets or magnetic metals. The first magnetic suction fitting piece, the second magnetic suction fitting piece, the third magnetic suction fitting piece, and the fourth magnetic suction fitting piece can be magnets or magnetic metals. When the first magnetic suction member, the second magnetic suction member, the third magnetic suction member, and the fourth magnetic suction member are magnets, the first magnetic suction fitting piece, the second magnetic suction fitting piece, the third magnetic suction fitting piece, and the fourth magnetic suction fitting piece are magnetic metals. When the first magnetic suction fitting piece, the second magnetic suction fitting piece, the third magnetic suction fitting piece, and the fourth magnetic suction fitting piece are magnets, the first magnetic suction member, the second magnetic suction member, the third magnetic suction member, and the fourth magnetic suction member are magnets or magnetic metals.

Figure 8:
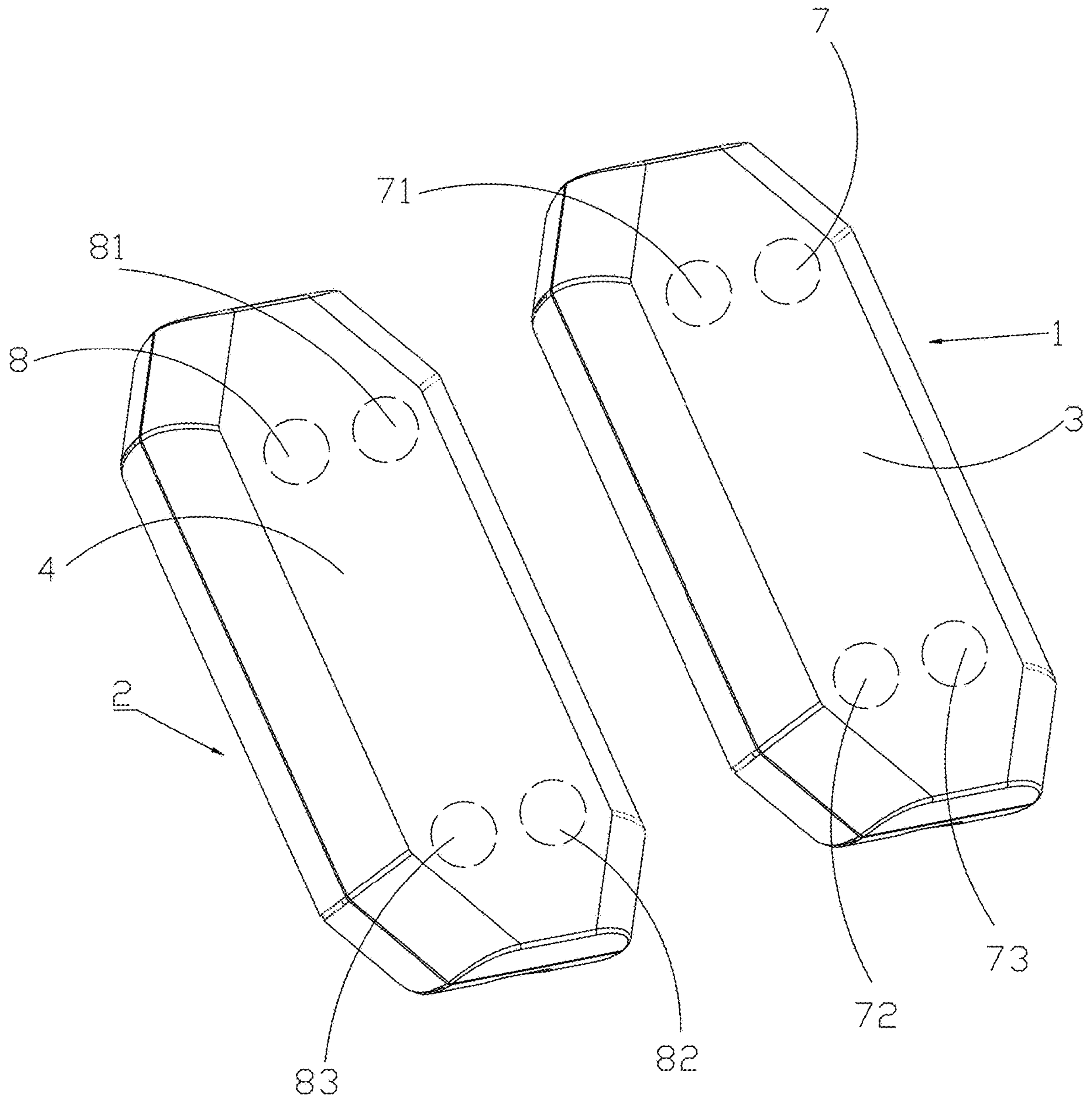
FIG. 8 is a schematic structural diagram of a first magnetic suction member, a second magnetic suction member, a third magnetic suction member, a fourth magnetic suction member, a first magnetic suction fitting piece, a second magnetic suction fitting piece, a third magnetic suction fitting piece, and a fourth magnetic suction fitting piece.
Figure 9:
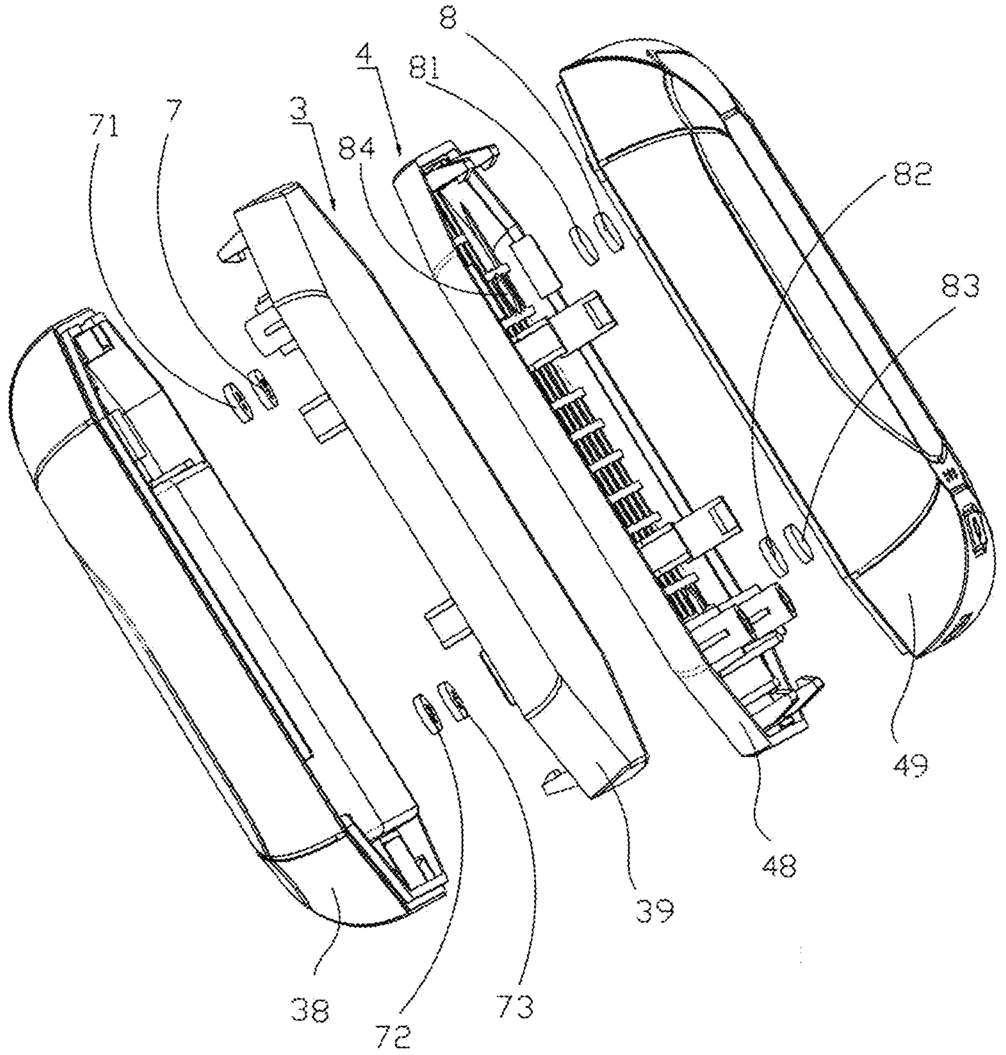
FIG. 9 is an exploded diagram of a first magnetic suction member, a second magnetic suction member, a third magnetic suction member, a fourth magnetic suction member, a first magnetic suction fitting piece, a second magnetic suction fitting piece, a third magnetic suction fitting piece, and a fourth magnetic suction fitting piece.
Figure 10:
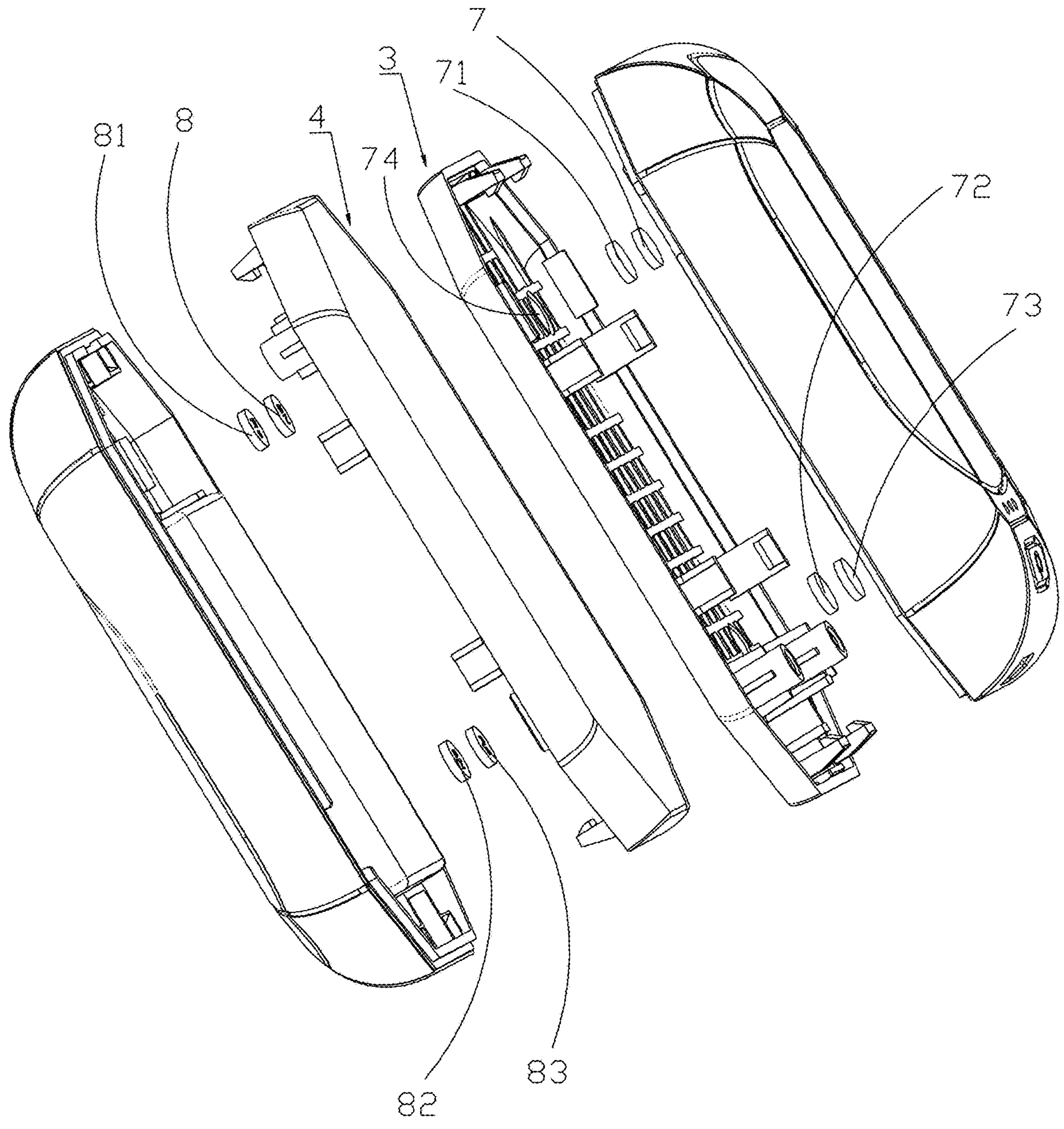
FIG. 10 is another exploded diagram of a first magnetic suction member, a second magnetic suction member, a third magnetic suction member, a fourth magnetic suction member, a first magnetic suction fitting piece, a second magnetic suction fitting piece, a third magnetic suction fitting piece, and a fourth magnetic suction fitting piece.
Figure 11:
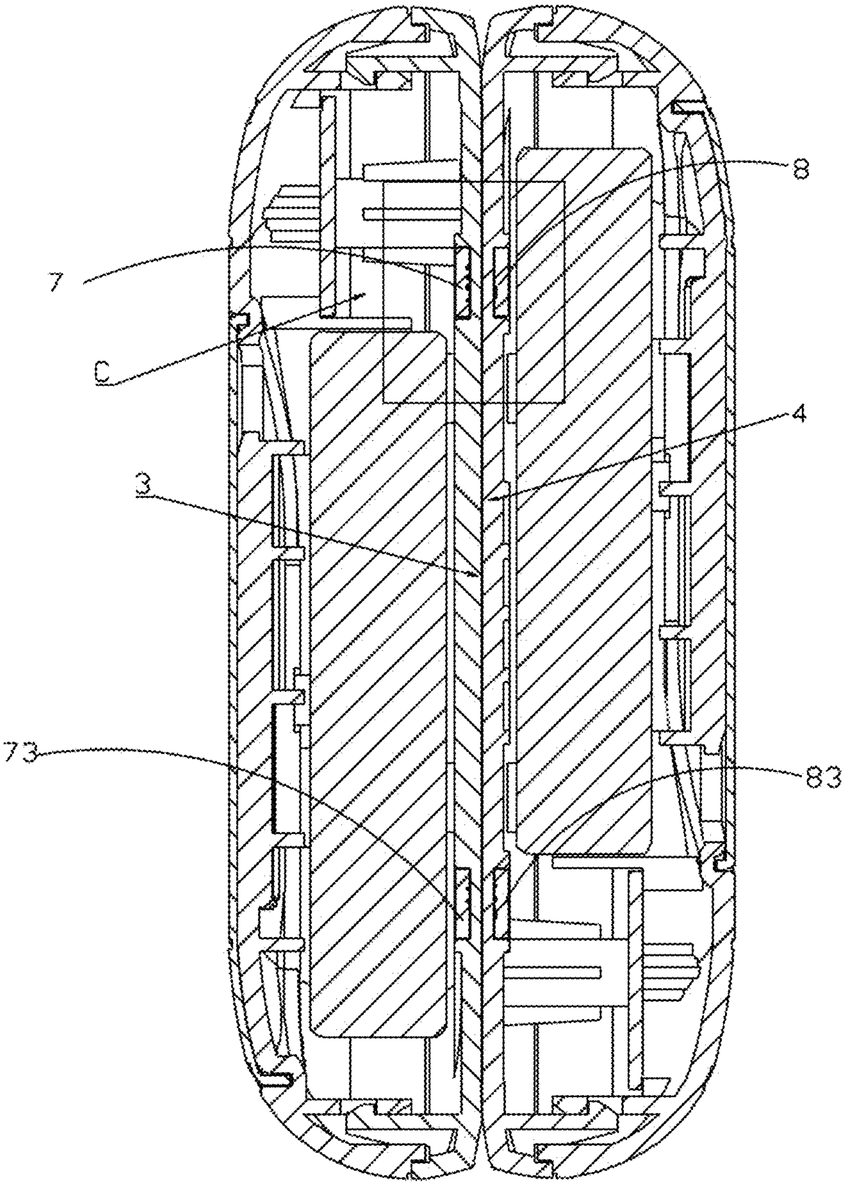
FIG. 11 is sectional view cut along a first magnetic suction member, a fourth magnetic suction member, a first magnetic suction fitting piece, and a fourth magnetic suction fitting piece.
Figure 12:
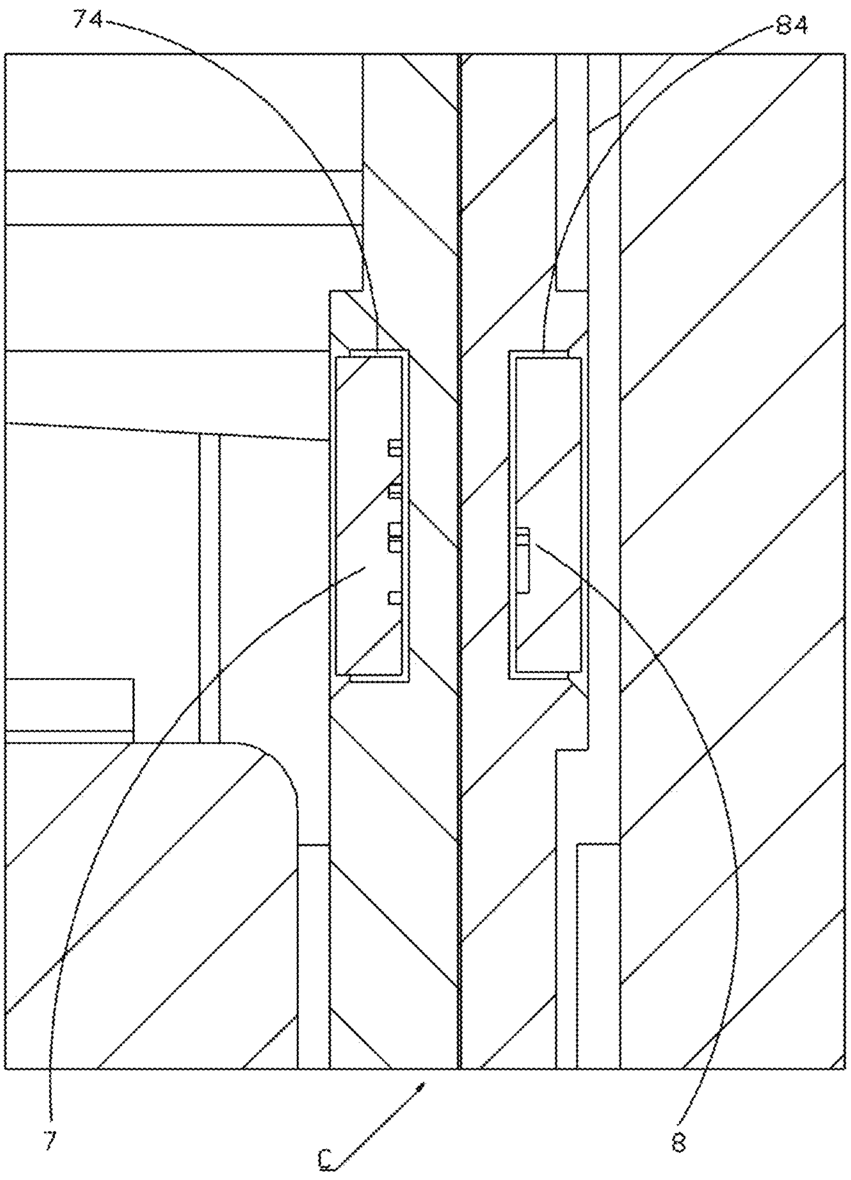
FIG. 12 is an enlarged view of the part C in FIG. 11.
Figure 13:
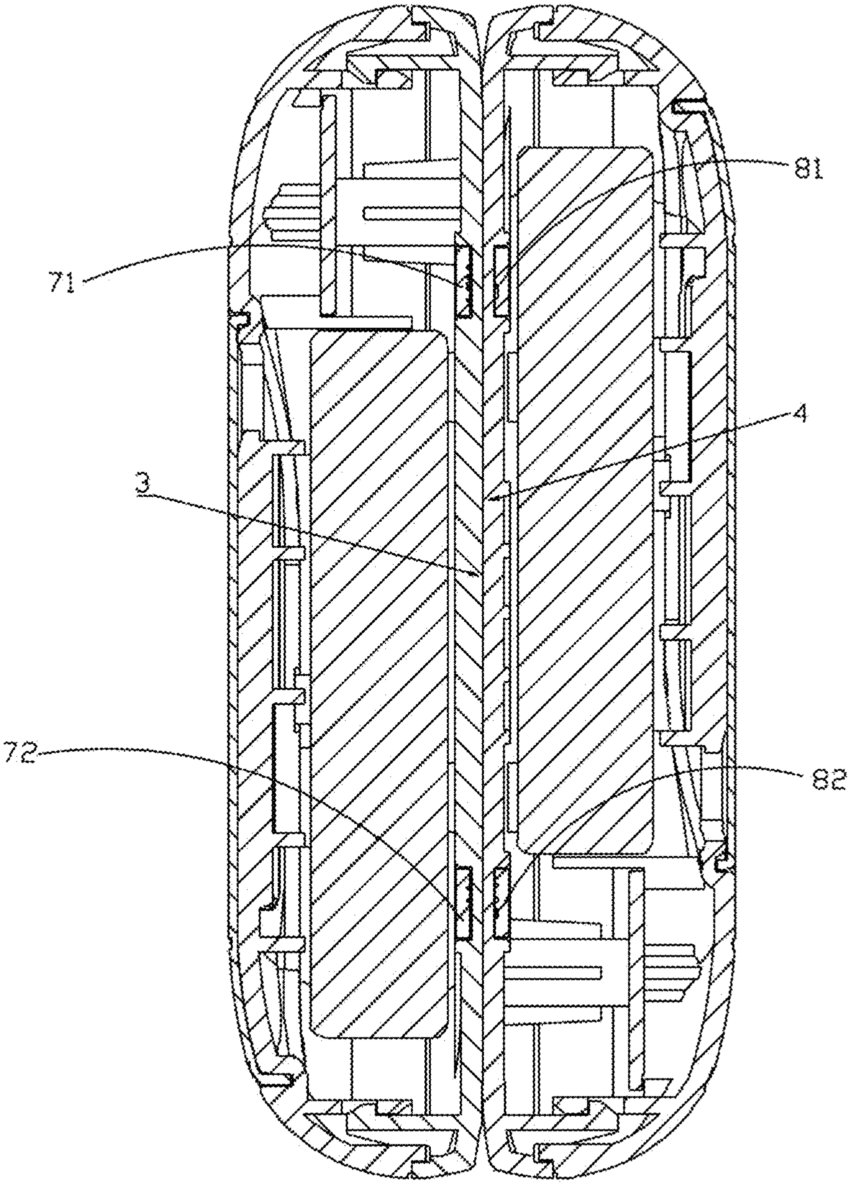
FIG. 13 is sectional view cut along a second magnetic suction member, a third magnetic suction member, a second magnetic suction fitting piece, and a third magnetic suction fitting piece.
Figure 14:
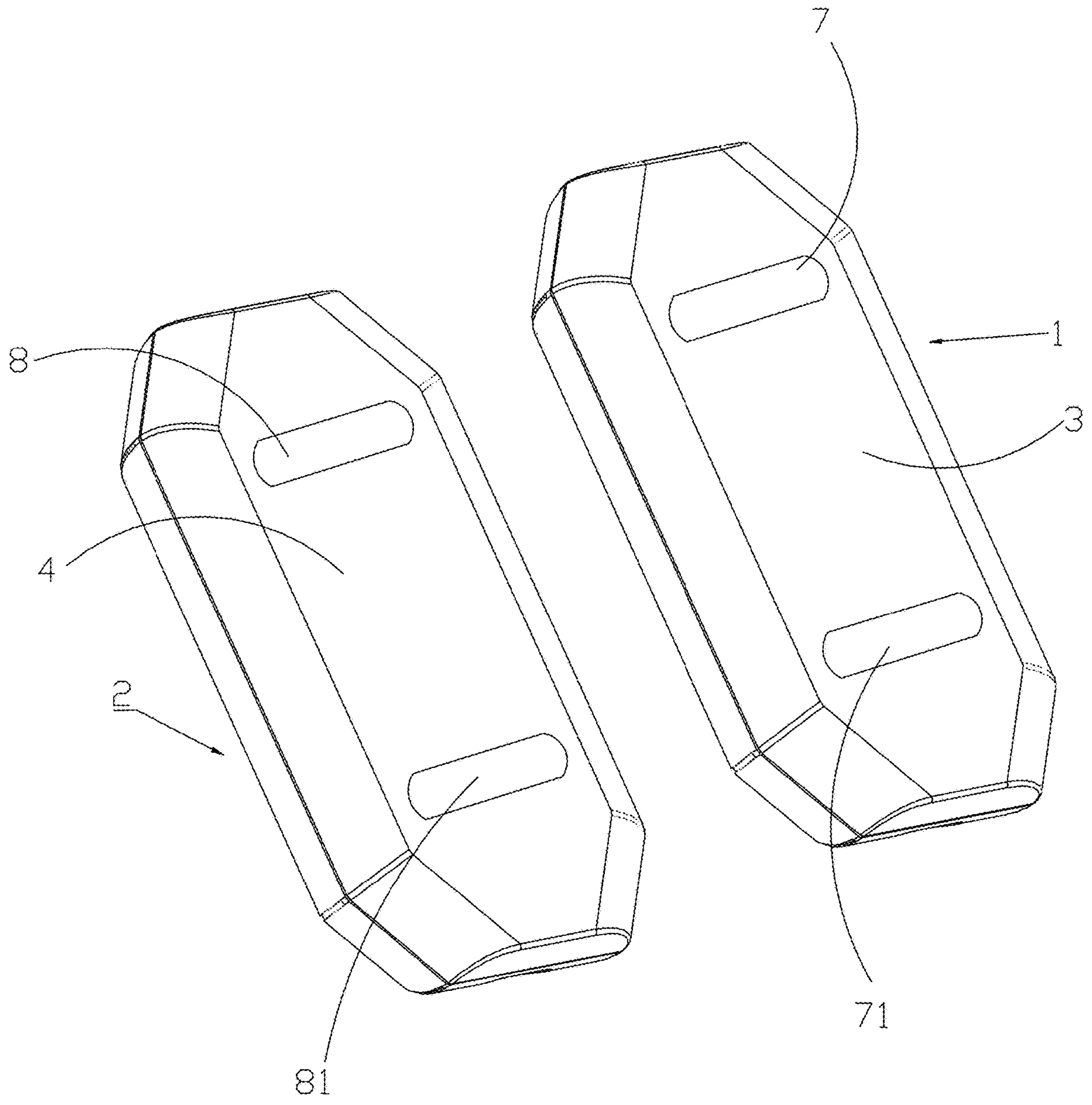
FIG. 14 is another exploded diagram of a first magnetic suction member, a second magnetic suction member, a third magnetic suction member, a fourth magnetic suction member, a first magnetic suction fitting piece, a second magnetic suction fitting piece, a third magnetic suction fitting piece, and a fourth magnetic suction fitting piece.

Referring to FIG. 8 and FIG. 14, the first magnetic suction member, the second magnetic suction member, the third magnetic suction member, the fourth magnetic suction member, the first magnetic suction fitting piece, the second magnetic suction fitting piece, the third magnetic suction fitting piece, and the fourth magnetic suction fitting piece can be circular magnetic suction members and magnetic suction fitting pieces, or may be magnetic suction members and magnetic suction fitting pieces in another geometric shape such as ellipse or square. The first magnetic suction member 7 is circular or elliptical; a length range of the first magnetic suction member 7 is 5-25 mm; a width range of the first magnetic suction member 7 is 5-25 mm; the first magnetic suction fitting piece 8 is circular or elliptical; a length range of the first magnetic suction fitting piece 8 is 5-25 mm; a width range of the first magnetic suction fitting piece 8 is 5-25 mm; or, the first magnetic suction member 7 is elongated; a length range of the first magnetic suction member 7 is 10-30 mm; a width range of the first magnetic suction member 7 is 3-10 mm; the first magnetic suction fitting piece 8 is elongated; a length range of the first magnetic suction fitting piece 8 is 10-30 mm; and a width range of the first magnetic suction fitting piece 8 is 3-10 mm. Specifically, an area of the first magnetic suction member 7 accounts for 5%-20% of an area of the first connecting inner surface 15, and an area of the first magnetic suction fitting piece 8 accounts for 5%-20% of an area of the second connecting inner surface 25. Through the above structure, the first magnetic suction member 7 is circular or elliptical; the length range of the first magnetic suction member 7 is 5-25 mm; the width range of the first magnetic suction member 7 is 5-25 mm; the first magnetic suction fitting piece 8 is circular or elliptical; the length range of the first magnetic suction fitting piece 8 is 5-25 mm; the width range of the first magnetic suction fitting piece 8 is 5-25 mm; or, the first magnetic suction member 7 is elongated; the length range of the first magnetic suction member 7 is 10-30 mm; the width range of the first magnetic suction member 7 is 3-10 mm; the first magnetic suction fitting piece 8 is elongated; the length range of the first magnetic suction fitting piece 8 is 10-30 mm; and the width range of the first magnetic suction fitting piece 8 is 3-10 mm. Specifically, the area of the first magnetic suction member 7 accounts for 5%-20% of the area of the first connecting inner surface 15, and the area of the first magnetic suction fitting piece 8 accounts for 5%-20% of an area of the second connecting inner surface 25. This makes the size and proportion design of the first magnetic suction member and the first magnetic suction fitting piece reasonable. The structure is simple, and the connection is stable, so that a magnetic suction force generated by the mutual magnetic suction between the first magnetic suction member and the first magnetic suction fitting piece can stably combine the first hand warmer unit 1 and the second hand warmer unit 2 into a whole, and a magnetic suction force generated by the mutual magnetic suction between the first magnetic suction member and the first magnetic suction fitting piece can effectively prevent the first hand warmer unit 1 from being separated from the second hand warmer unit 2. It is convenient for a user to combine the first hand warmer unit 1 and the second hand warmer unit 2 into a whole for hand warming. Even if the user swings the combined hand warmer during use, the first hand warmer unit 1 sand the second hand warmer unit 2 can be kept in a combined state, which greatly improves the user experience.

One or more implementation modes are provided above in combination with specific contents, and it is not deemed that the specific implementation of the present disclosure is limited to these specifications. Any technical deductions or replacements approximate or similar to the method and structure of the present disclosure or made under the concept of the present disclosure shall fall within the scope of protection of the present disclosure.

What is claimed is:

1. A combined hand warmer, comprising a first hand warmer unit (1) and a second hand warmer unit (2), wherein the first hand warmer unit (1) comprises a first outer surface (14) and a first connecting inner surface (15) opposite to the first outer surface (14); the second hand warmer unit comprises a second outer surface (24) and a second connecting inner surface (25) opposite to the second outer surface (24); the first connecting inner surface (15) comprises a first connecting portion (3); the second connecting inner surface (25) comprises a second connecting portion (4); and the first connecting portion (3) and the second connecting portion (4) are detachably connected to each other through a plurality of magnetic components, thus the first connecting inner surface (15) is detachably connected to the second connecting inner surface (25), thereby the first hand warmer unit (1) and the second hand warmer unit (2) are combined into a whole;

wherein the first hand warmer unit (1) comprises a first shell (38) and a second shell (39) assembled to the first shell (38), the second hand warmer unit (2) comprises a third shell (48) and a fourth shell (49) assembled to the third shell (48), the first outer surface (14) is formed on an outer surface of the first shell (38), the first connecting inner surface (15) is formed on an outer surface of the second shell (39), and an inner surface of the second shell (39) defines a first mounting hole (74); the second outer surface (24) is formed on an outer surface of the fourth shell (49), the second connecting inner surface (25) is formed on an outer surface of the third shell (48), and an inner surface of the third shell (48) defines a second mounting hole (84); the plurality of magnetic components comprises a first magnetic member (7) arranged in the first mounting hole (74), and a first magnetic fitting piece (8) arranged in the second mounting hole (84), the first magnetic member (7) and the first magnetic fitting piece (8) are spaced apart by the second shell (39) and the third shell (48) wherein the first connecting inner surface (15) and the second connecting inner surface (25) are continuous, and the first magnetic member (7) is capable of being magnetically connected to the first magnetic fitting piece (8), wherein the first connecting inner surface (15) is capable of being connected to the second connecting inner surface (25) through the plurality of magnetic components;

wherein each of the first hand warmer unit (1) and the second hand warmer unit (2) is plate-shaped and comprises a width, length, and thickness, the thickness being less than the length and the width of the respective hand warmer unit; wherein a first outer surface (14) of the first hand warmer unit (1) and a second outer surface (24) of the second hand warmer unit (2) are each defined by their respective length and width, each serving as a complete warming surface; whereby the combination of the first hand warmer unit (1) and the second hand warmer unit (2) provides a total warming surface area comprised of the first and second outer surfaces (14,24).

2. The combined hand warmer according to claim 1, wherein a second magnetic fitting piece (71) is further provided inside the inner surface of the second shell (39); a second magnetic member (81) is further provided inside the inner surface of the third shell (48); the second magnetic fitting piece (71) and the second magnetic member (81) are magnetically connected.

3. The combined hand warmer according to claim 2, wherein a third magnetic member (72) and a fourth magnetic fitting piece (73) is further provided inside the inner surface of the second shell (39); a third magnetic fitting piece (82) and a fourth magnetic member (83) are further provided inside the inner surface of the third shell (48); the third magnetic member (72) and the third magnetic fitting piece (82) are magnetically connected; and the fourth magnetic fitting piece (73) and the fourth magnetic member (83) are magnetically connected, so that the first connecting inner surface (15) is detachably connected to the second connecting inner surface (25).

4. The combined hand warmer according to claim 1, wherein the first magnetic member (7) is circular or elliptical; a length range of the first magnetic member (7) is 5-25 mm; a width range of the first magnetic member (7) is 5-25 mm; the first magnetic fitting piece (8) is circular or elliptical; a length range of the first magnetic fitting piece (8) is 5-25 mm; a width range of the first magnetic fitting piece (8) is 5-25 mm; or, the first magnetic member (7) is elongated; a length range of the first magnetic member (7) is 10-30 mm; a width range of the first magnetic member (7) is 3-10 mm; the first magnetic fitting piece (8) is elongated; a length range of the first magnetic fitting piece (8) is 10-30 mm; and a width range of the first magnetic fitting piece (8) is 3-10 mm.

5. The combined hand warmer according to claim 1, wherein an area of the first magnetic member (7) accounts for 5%-20% of an area of the first connecting inner surface (15), and an area of the first magnetic fitting piece (8) accounts for 5%-20% of an area of the second connecting inner surface (25).

6. The combined hand warmer according to claim 1, wherein the first connecting inner surface (15) and the second connecting inner surface (25) are continuous without interrupted element, and buttons are located on the first outer surface (14) and the second outer surface (24).

7. A combined hand warmer, comprising a first hand warmer unit (1) and a second hand warmer unit (2), wherein the first hand warmer unit (1) comprises a first outer surface (14) and a first connecting inner surface (15) opposite to the first outer surface (14); the second hand warmer unit comprises a second outer surface (24) and a second connecting inner surface (25) opposite to the second outer surface (24); the first connecting inner surface (15) is detachably connected to the second connecting inner surface (25) through a plurality of magnetic components, thereby the first hand warmer unit (1) and the second hand warmer unit (2) are combined into a whole, wherein the first hand warmer unit (1) is connected to the second hand warmer unit (2) to form a combination in a manner that the first outer surface (14) is opposite to the second outer surface (24), the plurality of magnetic components comprises a first magnetic member (7) and a second magnetic fitting piece (71) located inside the first hand warmer unit (1), and a first magnetic fitting piece (8) and a second magnetic member (81) located inside the second hand warmer unit (2), wherein the first magnetic member (7) and the second magnetic fitting piece (71), and the first magnetic fitting piece (8) and the second magnetic member (81), are spaced apart by the first connecting inner surface (15) and the second connecting inner surface (25) wherein the first connecting inner surface (15) and the second connecting inner surface (25) are uninterrupted;

wherein each of the first hand warmer unit (1) and the second hand warmer unit (2) is plate-shaped and comprises a width, length, and thickness, the thickness being less than the length and the width of the respective hand warmer unit; wherein a first outer surface (14) of the first hand warmer unit (1) and a second outer surface (24) of the second hand warmer unit (2) are each defined by their respective length and width, each serving as a complete warming surface; whereby the combination of the first hand warmer unit (1) and the second hand warmer unit (2) provides a total warming surface area comprised of the first and second outer surfaces (14,24).

8. The combined hand warmer according to claim 7, wherein the first connecting inner surface (15) and the second connecting inner surface (25) are uninterrupted without exposed elements, and buttons are located on the first outer surface (14) and the second outer surface (24).

9. The combined hand warmer according to claim 7, wherein the plurality of magnetic components cooperatively account for 5%-20% of an area of the first connecting inner surface (15), and the plurality of magnetic components cooperatively account for 5%-20% of an area of the second connecting inner surface (25).

* * * * *